(12) United States Patent
Humair

(10) Patent No.: US 12,622,781 B2
(45) Date of Patent: May 12, 2026

(54) TISSUE BASED BIOPROSTHETIC HEART VALVE

(71) Applicant: Boston Scientific Limited, Hamilton (BM)

(72) Inventor: Arnaud Humair, Mont-sur-Rolle (CH)

(73) Assignee: Boston Scientific Limited, Hamilton (BM)

( * ) Notice: Subject to any disclaimer, the term of this patent is extended or adjusted under 35 U.S.C. 154(b) by 880 days.

(21) Appl. No.: 17/948,669

(22) Filed: Sep. 20, 2022

(65) Prior Publication Data

US 2023/0055399 A1      Feb. 23, 2023

Related U.S. Application Data

(63) Continuation of application No. 17/011,366, filed on Sep. 3, 2020, now abandoned.

(60) Provisional application No. 62/899,405, filed on Sep. 12, 2019.

(51) Int. Cl.
*A61F 2/24* (2006.01)
*A61L 27/36* (2006.01)

(52) U.S. Cl.
CPC .......... *A61F 2/2418* (2013.01); *A61F 2/2415* (2013.01); *A61F 2/2436* (2013.01); *A61L 27/3687* (2013.01); *A61F 2240/001* (2013.01); *A61L 2430/40* (2013.01)

(58) Field of Classification Search
None
See application file for complete search history.

(56) References Cited

U.S. PATENT DOCUMENTS

| | | | |
|---|---|---|---|
| 8,361,144 B2 | 1/2013 | Fish et al. | |
| 9,333,075 B2 | 5/2016 | Biadillah et al. | |
| 9,414,915 B2 | 8/2016 | Lombardi et al. | |
| 9,498,317 B2 | 11/2016 | Gautam et al. | |
| 10,258,464 B2 | 4/2019 | Delaloye et al. | |
| 2007/0154515 A1* | 7/2007 | Johnson .............. A61L 27/3645 |
| | | | 424/423 |

(Continued)

FOREIGN PATENT DOCUMENTS

WO      2017040684      3/2017

OTHER PUBLICATIONS

"Office Action," for Japanese Patent Application No. 2022-516030 mailed Mar. 22, 2023 (10 pages), with English translation.

(Continued)

*Primary Examiner* — Mohammad M Ameen
(74) *Attorney, Agent, or Firm* — Pauly, DeVries Smith & Deffner LLC

(57)                    ABSTRACT

Embodiments herein relate to bioprosthetic heart valves. In an embodiment, a heart valve replacement system is included having a delivery catheter can include a heart valve accommodation region; and a heart valve disposed around the delivery catheter at the heart valve accommodation region of the delivery catheter, the heart valve can include a frame; and a plurality of valve leaflets coupled to the frame; wherein the valve leaflets include an animal tissue, the animal tissue can include from 15% to 50% by weight water; and from 20% to 70% by weight glycerol; a package defining an interior volume, wherein the delivery catheter and the heart valve are disposed within the package. Other embodiments are also included herein.

20 Claims, 13 Drawing Sheets

(56) References Cited

U.S. PATENT DOCUMENTS

| | | | |
|---|---|---|---|
| 2008/0102439 A1 | 5/2008 | Tian et al. | |
| 2008/0177381 A1 | 7/2008 | Navia et al. | |
| 2010/0030340 A1 | 2/2010 | Wolfinbarger et al. | |
| 2011/0301700 A1* | 12/2011 | Fish | A61F 2/2418 |
| | | | 156/60 |
| 2012/0016468 A1* | 1/2012 | Robin | A61F 2/2427 |
| | | | 623/2.11 |
| 2013/0158658 A1 | 6/2013 | Hayzlett | |
| 2013/0325111 A1 | 12/2013 | Campbell et al. | |
| 2013/0332511 A1 | 12/2013 | Hala et al. | |
| 2015/0282930 A1* | 10/2015 | Lehenberger | A61L 27/3625 |
| | | | 623/2.11 |
| 2017/0056149 A1* | 3/2017 | Rajpara | A61F 2/9525 |
| 2019/0224369 A1 | 7/2019 | Rzany et al. | |
| 2021/0077253 A1 | 3/2021 | Humair | |

OTHER PUBLICATIONS

File History for U.S. Appl. No. 17/011,366 downloaded Oct. 21, 2022 (215 pages).

"International Preliminary Report on Patentability," for PCT Application No. PCT/EP2020/075495 mailed Mar. 24, 2022 (9 pages).

"International Search Report and Written Opinion," for PCT Application No. PCT/EP2020/075495 mailed Nov. 30, 2020 (12 pages).

"Response to Communication Pursuant to Rules 161(1) and 162 EPC," for European Patent Application No. 20775587.7 filed Oct. 20, 2022 (14 pages).

"Communication pursuant to Article 94(3)," for European Patent Application No. 20775587.7 mailed May 12, 2025 (6 pages).

"First Office Action," for CN Patent Application No. 202080063548. 4, mailed Aug. 2, 2024, 15 pages, with English summary.

* cited by examiner

1302

1304

Cutting animal
tissue into leaflets

1306

Coupling the
leaflets to a frame

1308

Contacting the
leaflets with a
composition

1310

Removing
moisture from the
leaflets

1312

Placing the heart
valve onto a
delivery catheter

1314

At least partially
crimping the heart
valve onto the
delivery catheter

TISSUE BASED BIOPROSTHETIC HEART VALVE

This application is a continuation application of U.S. patent application Ser. No. 17/011,366, filed on Sep. 3, 2020, which claims the benefit of U.S. Provisional Application No. 62/899,405, filed Sep. 12, 2019, the content of which is herein incorporated by reference in its entirety.

FIELD

Embodiments herein relate to bioprosthetic heart valves. More specifically, embodiments herein relate to percutaneously deliverable bioprosthetic heart valves.

BACKGROUND

Heart function can be significantly impaired when a heart valve is not functioning properly. Potential causes for heart valve malfunction include dilation of an annulus around the valve, ventricular dilation, a prolapsed or misshapen valve leaflet, and stenosis, such as aortic stenosis. When the heart valve is unable to close properly, the blood within a heart chamber can regurgitate, or leak backwards through the valve. When the heart valve is unable to open properly, forward blood flow (e.g. systolic blood flow) can be impaired.

Valve malfunction may be treated by replacing or repairing a diseased valve, such as an aortic valve. Surgical valve replacement is one method for treating the diseased valve. Minimally invasive methods of treatment, such as transcatheter aortic valve replacement (TAVR), generally involve the use of delivery catheters that are delivered through arterial passageways or other anatomical routes into the heart to replace the diseased valve with an implantable prosthetic heart valve. Leaflets of such valves have been formed from various materials including synthetic materials and animal tissues.

SUMMARY

In a first aspect, a heart valve replacement system is included having a delivery catheter and a heart valve. The delivery catheter can include a heart valve accommodation region. A heart valve can be disposed around the delivery catheter at the heart valve accommodation region of the delivery catheter. The heart valve can include a frame and a plurality of valve leaflets coupled to the frame. The valve leaflets can include an animal tissue. The animal tissue can include from 15% to 50% by weight water; and from 20% to 70% by weight glycerol. The heart valve replacement system can further include a package defining an interior volume. The delivery catheter and the heart valve can be disposed within the package.

In a second aspect, in addition to one or more of the preceding or following aspects, or in the alternative to some aspects, the animal tissue further can include at least about 0.15% by weight of a cation of a salt. The cation can be selected from the group consisting of sodium, potassium, calcium and magnesium.

In a third aspect, in addition to one or more of the preceding or following aspects, or in the alternative to some aspects, further can include a sheath disposed at least partly over the heart valve. The sheath can have an inner diameter of 18 F or smaller.

In a fourth aspect, in addition to one or more of the preceding or following aspects, or in the alternative to some aspects, the heart valve is uncrimped onto the delivery catheter and has an outside waist diameter of greater than 20 mm as disposed around the delivery catheter within the package.

In a fifth aspect, in addition to one or more of the preceding or following aspects, or in the alternative to some aspects, the heart valve is partially crimped onto the delivery catheter and has an outside waist diameter of from 19 mm to 10 mm as disposed around the delivery catheter within the package.

In a sixth aspect, in addition to one or more of the preceding or following aspects, or in the alternative to some aspects, the heart valve is crimped onto the delivery catheter and has an outside waist diameter of less than 7 mm as disposed around the delivery catheter within the package.

In a seventh aspect, in addition to one or more of the preceding or following aspects, or in the alternative to some aspects, the animal tissue can include from 15 to 60% by weight glycerol.

In an eighth aspect, in addition to one or more of the preceding or following aspects, or in the alternative to some aspects, the heart valve further can include a skirt, the skirt can include an animal tissue, the animal tissue can include from 15% to 50% by weight water; and from 20% to 70% by weight glycerol.

In a ninth aspect, a method of making a heart valve replacement device is included. The method can include cutting animal tissue into leaflets; coupling the leaflets to a frame to form a heart valve; contacting the leaflets with a composition can include glycerol; removing moisture from the leaflets in an environment at above room temperature and/or below atmospheric pressure; and placing the heart valve on a delivery catheter.

In a tenth aspect, in addition to one or more of the preceding or following aspects, or in the alternative to some aspects, the composition includes a glycerol and water mixture.

In an eleventh aspect, in addition to one or more of the preceding or following aspects, or in the alternative to some aspects, the composition includes a glycerol, water and sodium mixture.

In a twelfth aspect, in addition to one or more of the preceding or following aspects, or in the alternative to some aspects, the composition includes a glycerol and ethanol mixture.

In a thirteenth aspect, in addition to one or more of the preceding or following aspects, or in the alternative to some aspects, the composition includes a glycerol, water and ethanol mixture.

In a fourteenth aspect, in addition to one or more of the preceding or following aspects, or in the alternative to some aspects, further can include partially crimping the heart valve onto the delivery catheter.

In a fifteenth aspect, in addition to one or more of the preceding or following aspects, or in the alternative to some aspects, further can include fully crimping the heart valve onto the delivery catheter.

In a sixteenth aspect, in addition to one or more of the preceding or following aspects, or in the alternative to some aspects, further can include packaging the heart valve and the delivery catheter, wherein the heart valve remains uncrimped prior to packaging of the heart valve and delivery catheter.

In a seventeenth aspect, in addition to one or more of the preceding or following aspects, or in the alternative to some aspects, the operation of contacting the leaflets with a composition can include glycerol and drying the leaflets is performed before the step of attaching the leaflets to a frame to form a heart valve.

In an eighteenth aspect, in addition to one or more of the preceding or following aspects, or in the alternative to some aspects, the leaflets can have a water content of about 15 to 50 wt. % and a glycerol content of about 20 to about 70 wt. % after removing moisture.

In a nineteenth aspect, in addition to one or more of the preceding or following aspects, or in the alternative to some aspects, further can include packaging the heart valve and the delivery catheter. The leaflets can have a water content of about 15 to about 50 wt. % and a glycerol content of about 20 to about 70 wt. % after being packaged.

In a twentieth aspect, in addition to one or more of the preceding or following aspects, or in the alternative to some aspects, further can include coupling a skirt to the frame; contacting the skirt with a composition can include glycerol; removing moisture from the skirt in an environment at above room temperature and/or below atmospheric pressure.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following figures (FIGS.), in which.

While embodiments are susceptible to various modifications and alternative forms, specifics thereof have been shown by way of example and drawings, and will be described in detail. It should be understood, however, that the scope herein is not limited to the particular aspects described. On the contrary, the intention is to cover modifications, equivalents, and alternatives falling within the spirit and scope herein.

DETAILED DESCRIPTION

Described herein are devices, systems, and methods associated with bioprosthetic heart valves. Various embodiments include a dehydration process of a bioprosthetic heart valve, and the resulting devices and systems. Various embodiments provide a heart valve pre-attached to a minimally invasive delivery system, optionally at least partially (e.g. completely) preloaded within the delivery system, that can be ready to use after sterilization with little or no preparation in an operating room. Some embodiments provide the ability to store a substantially dry and substantially glutaraldehyde-free heart valve that is pre-attached to, and optionally at least partly preloaded inside, a delivery system. The dehydration process can include the use of glycerol. In some embodiments, the water in the tissue for the heart valve can be replaced with a glycerol and/or saline solution.

Figure 1:
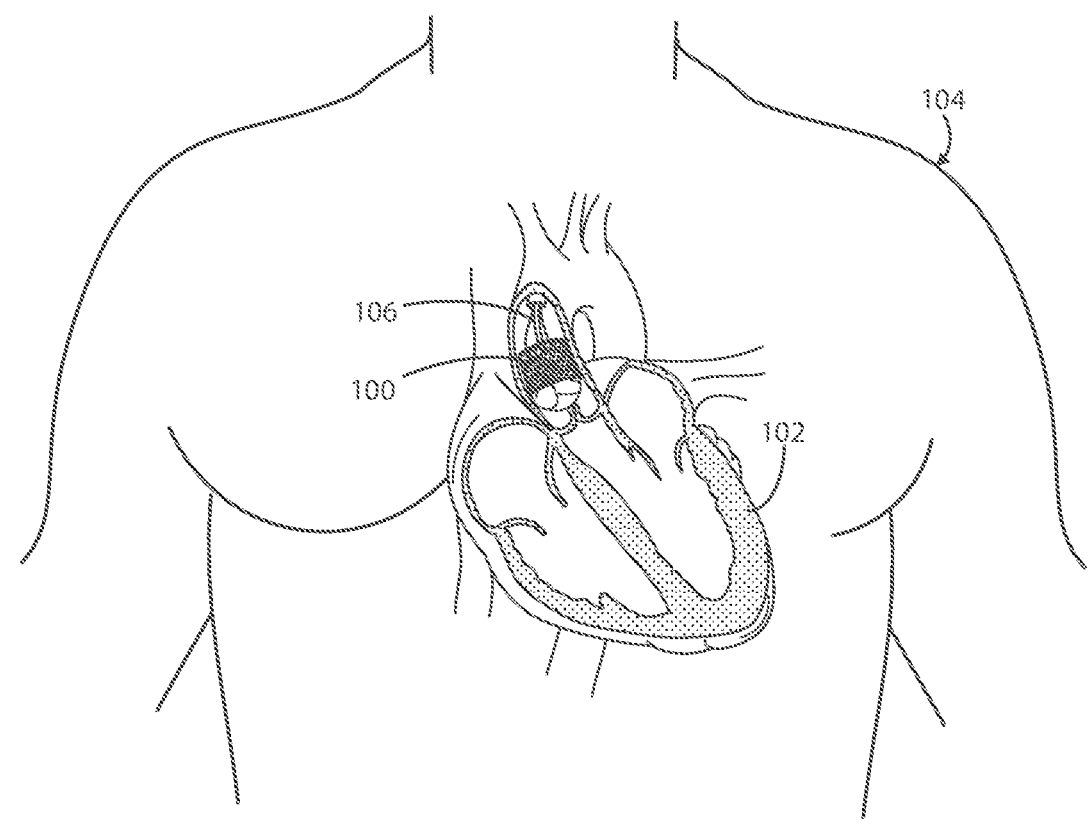
FIG. 1 is a schematic view of a prosthetic heart valve within a human body in accordance with various embodiments herein.

Referring now to FIG. 1, a schematic view of a prosthetic heart valve 100 within a heart 102 of a human body 104 is shown in accordance with various embodiments herein. The heart has four heart valves: a pulmonary valve, a tricuspid valve, an aortic valve and a mitral valve. The heart valves allow blood to pass through the heart and into major blood vessels connected to the heart, for example, the aorta and pulmonary artery. Prosthetic heart valve 100 of FIG. 1 can be surgically implanted or delivered through blood vessels using a delivery device or catheter 106. The delivery catheter 106 can be inserted into a femoral, subclavian, or an aortic incision during a transcatheter aortic valve replacement (TAVR) procedure. In various embodiments, the delivery catheter 106 can include a transfemoral delivery catheter 106. Once inserted, the delivery catheter 106 can deliver the prosthetic heart valve 100 to the desired location within the anatomy and release the heart valve 100 at a desired implantation site. Although FIG. 1 shows prosthetic heart valve 100 replacing an aortic valve, in some cases, prosthetic heart valve 100 can be a replacement for another type of heart valve (e.g., a mitral valve or a tricuspid valve). In some examples the heart valve is specifically a TAVI (transcatheter aortic valve implantation) valve.

Figure 8:
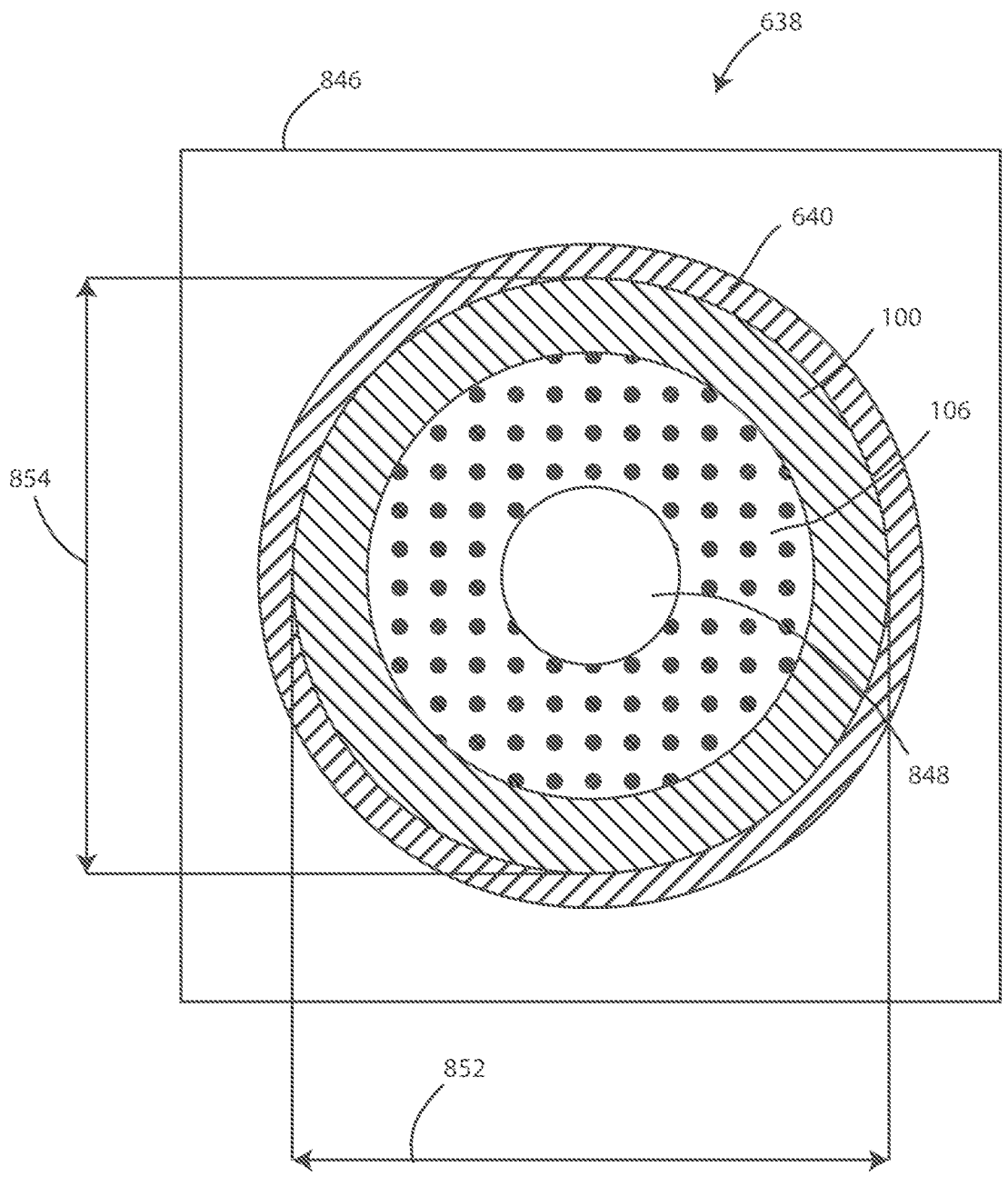
FIG. 8 is a schematic cross-sectional illustrative view of a heart valve replacement system in accordance with various embodiments herein.
Figure 9:
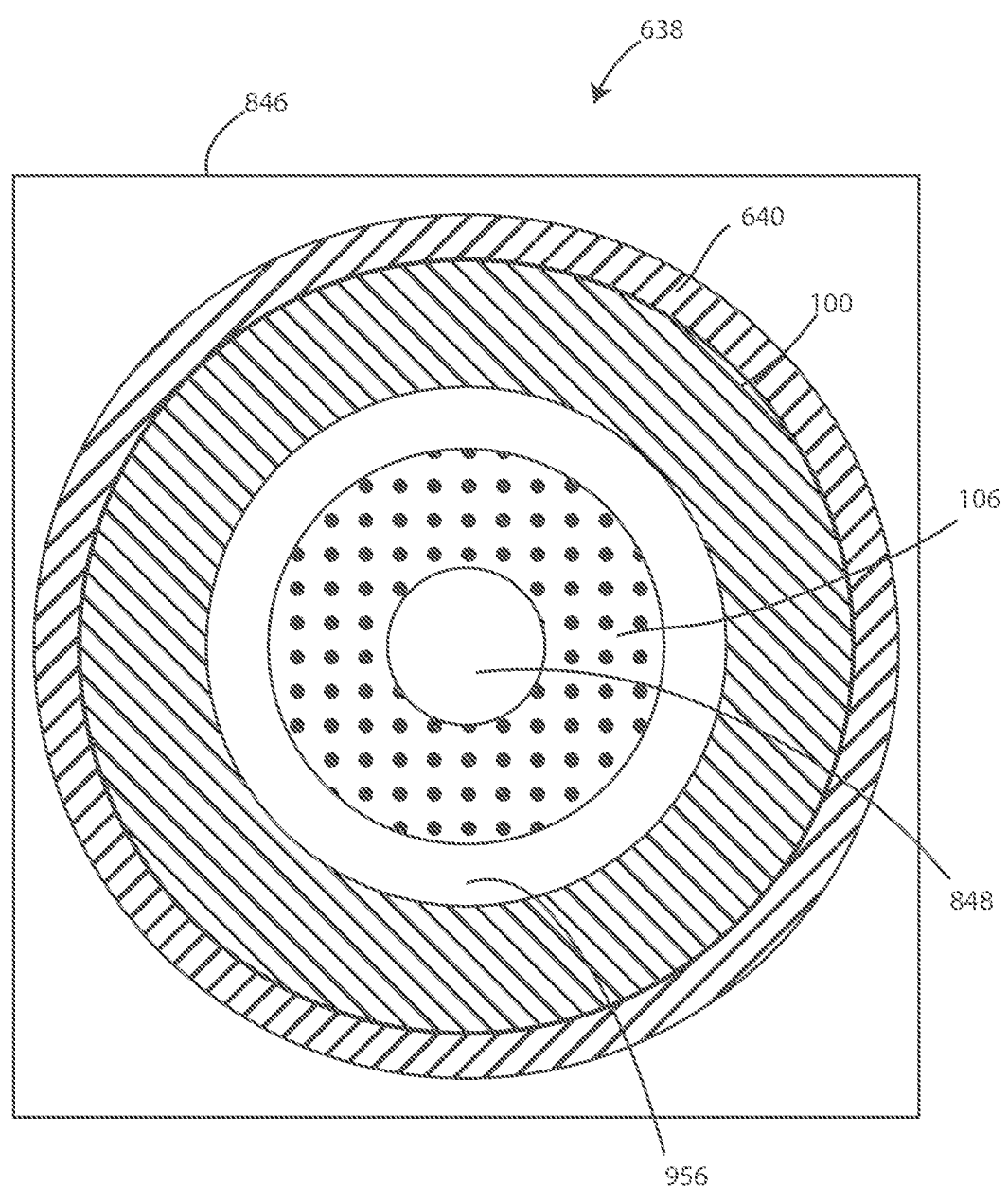
FIG. 9 is a schematic cross-sectional illustrative view of a heart valve replacement system in accordance with various embodiments herein.
Figure 10:
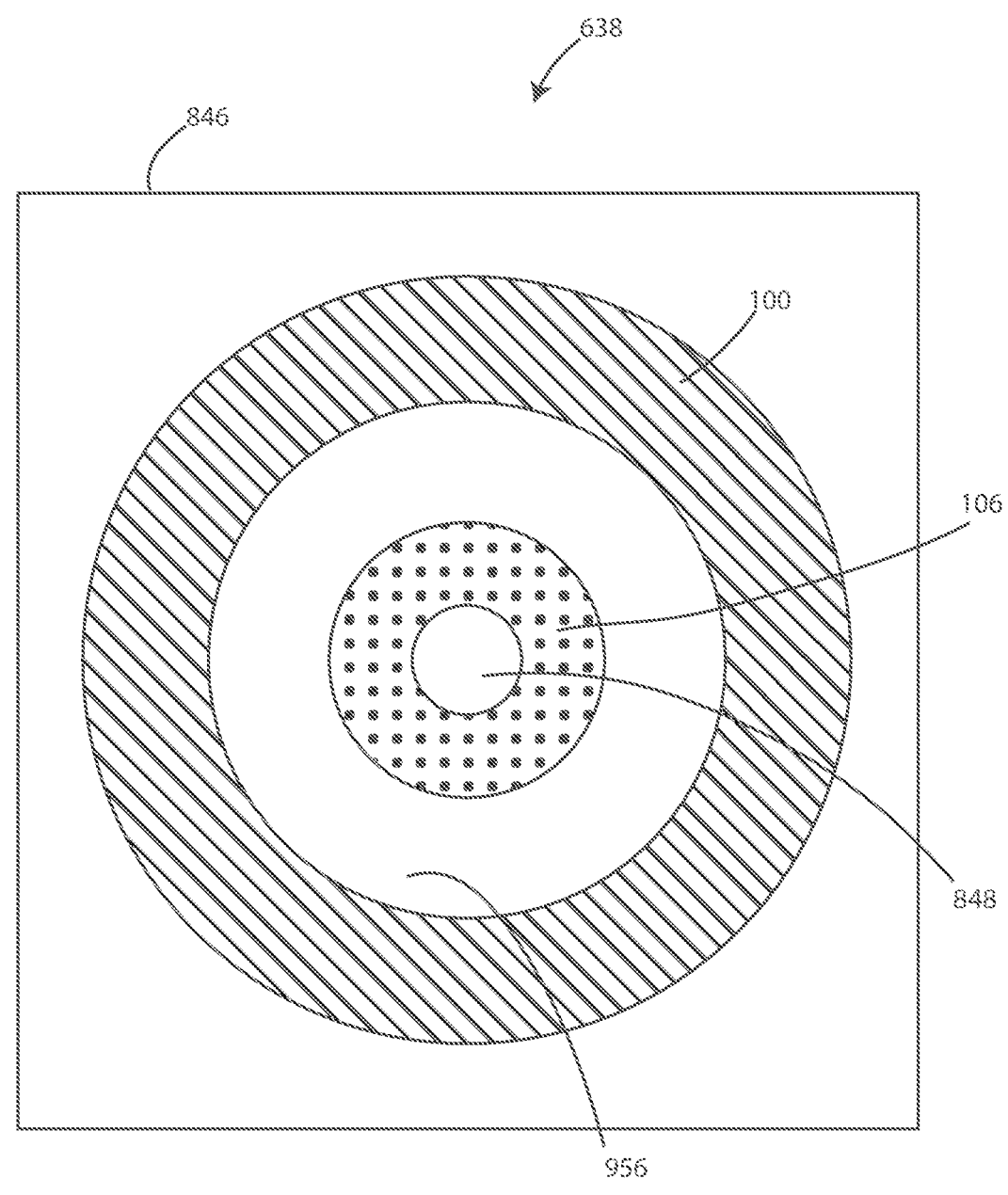
FIG. 10 is a schematic cross-sectional illustrative view of a heart valve replacement system in accordance with various embodiments herein.

A heart valve replacement system (not shown in this view) can include a heart valve 100 and a delivery catheter 106. In various embodiments, the delivery catheter 106 and the heart valve 100 are disposed within a sterile package (described further below). In various embodiments, the heart valve 100 can be disposed around a portion of the delivery catheter 106. In various embodiments, the heart valve 100 or a portion thereof can be fully crimped onto the delivery catheter 106, such as shown in FIG. 8. In various embodiments, the heart valve 100 or a portion thereof can be partially crimped onto the delivery catheter 106, such as shown in FIG. 9. In various embodiments, the heart valve 100 or a portion thereof can be uncrimped onto the delivery catheter 106, such as shown in FIG. 10. In some embodiments, a portion of the heart valve 100 can be crimped onto the delivery catheter 106 and a portion of the heart valve 100 can be uncrimped onto the delivery catheter 106. (It will be appreciated that FIGS. 8-10 are shown as simplified schematic views for ease and clarity of illustration.) In some embodiments, an uncrimped heart valve 100 can be attached or hooked onto a portion of the delivery catheter 106. In some embodiments, an uncrimped heart valve 100 can be in a controlled position relative to the delivery catheter 106.

Figure 2:
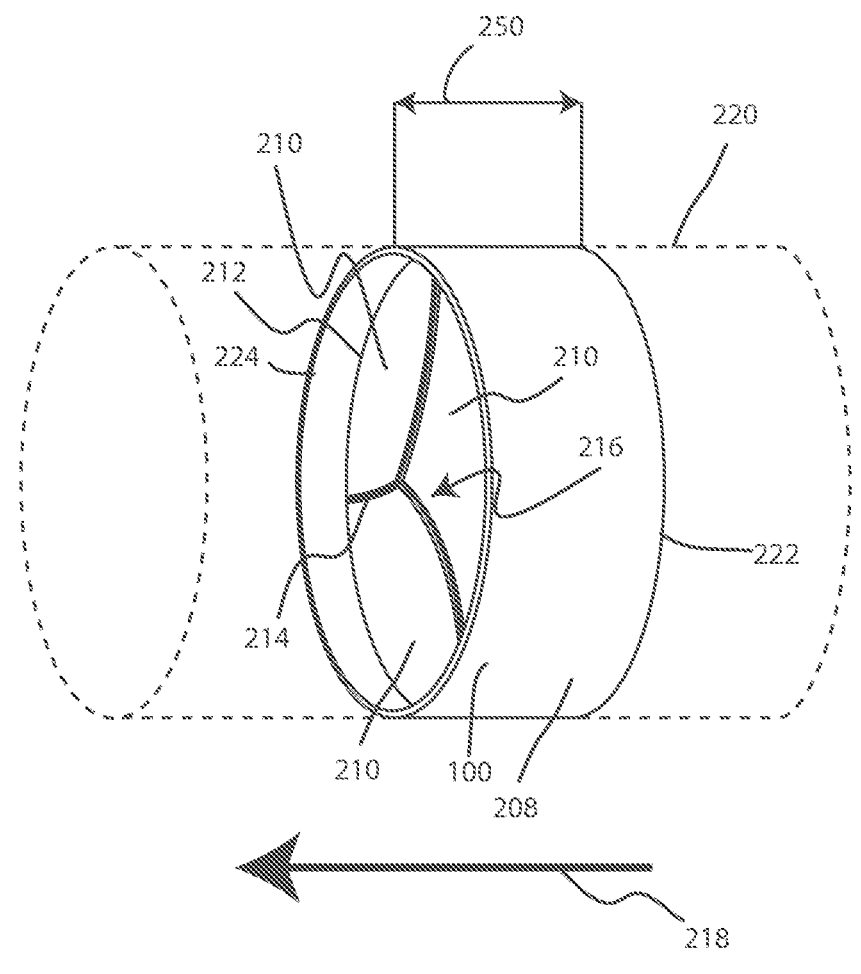
FIG. 2 is a schematic view of a prosthetic heart valve in a vessel in accordance with various embodiments herein.
Figure 3:
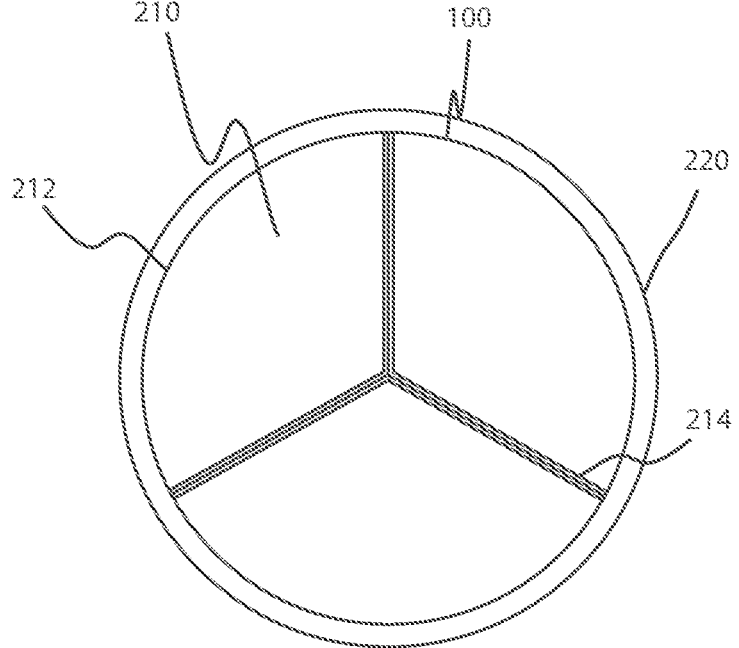
FIG. 3 is an end view of a prosthetic heart valve in accordance with various embodiments herein.

FIG. 2 shows a schematic view of a closed heart valve 100 in a vessel 220, according to various embodiments. FIG. 3 shows an end view of the closed heart valve 100. The valve 100 can be configured to allow one-way flow through the valve 100, such as depicted by arrow 218. In an embodiment, the arrow 218 represents blood flow during systole. The heart valve 100 can include an inlet 222 and an outlet 224.

In various embodiments, the heart valve 100 includes a frame 208. The frame 208 can define a central lumen which, in some embodiments, can be substantially cylindrical. The side of the frame 208 and other components facing the central lumen can be referred to as the luminal surface or luminal side. The opposite side of the frame 208 and other components (e.g., facing away from the central lumen) can be referred to as the abluminal surface or abluminal side. In various embodiments, the frame 208 can have a substantially circular cross-section. In other embodiments, the frame 208 can have a non-circular, such as a D-shaped, cross-section. In some embodiments, a non-circular frame 208 can be used to repair a mitral valve or another non-circular valve in the body.

The heart valve 100 can also include a plurality of valve leaflets 210, such as two or three leaflets 210. The heart valve 100 can include a coaptation region 216, such as where one or more leaflets 210 meet to close the valve 100 or separate to open the valve 100. In various embodiments, the valve leaflets 210 are coupled directly or indirectly to the frame 208, e.g. for support by the frame 208. The valve leaflets 210 can include a root edge 212, such as an edge of the leaflet 210 that is coupled to or adjacent to the frame 208. The valve leaflets 210 can also include a coaptation edge 214, such as an edge that aligns with an edge of an adjacent valve leaflet 210. The coaptation edge 214 can be movable relative to the root edge 212 to coapt with the coaptation edges 214 of the other leaflets 210. The coaptation edges 214 of the leaflets 210 move into coaptation with one another in a closed position (FIGS. 2 and 3) to substantially restrict fluid from flowing past the valve 100 in a direction opposite to arrow 218. Specifically, the leaflets 210 can coapt to fill up or close the central lumen of the valve 100 thereby impeding the flow of fluid opposite to arrow 218.

The heart valve 100 can have a longitudinal length 250. The longitudinal length 250 can have a length of various dimensions. In some embodiments, the length can be greater than or equal to 20 mm, 22 mm, 24 mm, 26 mm, 28 mm, 30 mm, 32 mm, 35 mm, 38 mm, 40 mm, 42 mm, 45 mm, 48 mm, or 50 mm. In some embodiments, the length can be less than or equal to 70 mm, 68 mm, 65 mm, 62 mm, 60 mm, 58 mm, 55 mm, 52 mm, or 50 mm. In some embodiments, the length can fall within a range of 20 mm to 70 mm, or 24 mm to 68 mm, or 30 mm to 65 mm, or 35 mm to 62 mm, or 40 mm to 60 mm, or 42 mm to 58 mm, or 45 mm to 55 mm, or 48 mm to 52 mm, or can be about 50 mm.

In various embodiments, the inner diameter of the central lumen can be at least 10 mm and not more than 50 mm. In various embodiments, the inner diameter of the central lumen can be at least 15 mm and not more than 40 mm. In various embodiments, the inner diameter of the central lumen can be at least 20 mm and not more than 35 mm.

Referring now to FIG. 3, an end view of a prosthetic heart valve 100 is shown in accordance with various embodiments herein. A heart valve replacement system (not shown in this view) includes a heart valve 100. The heart valve 100 can include a plurality of valve leaflets 210. The valve leaflets 210 can include a root edge 212. The valve leaflets 210 can also include a coaptation edge 214.

Figure 4:
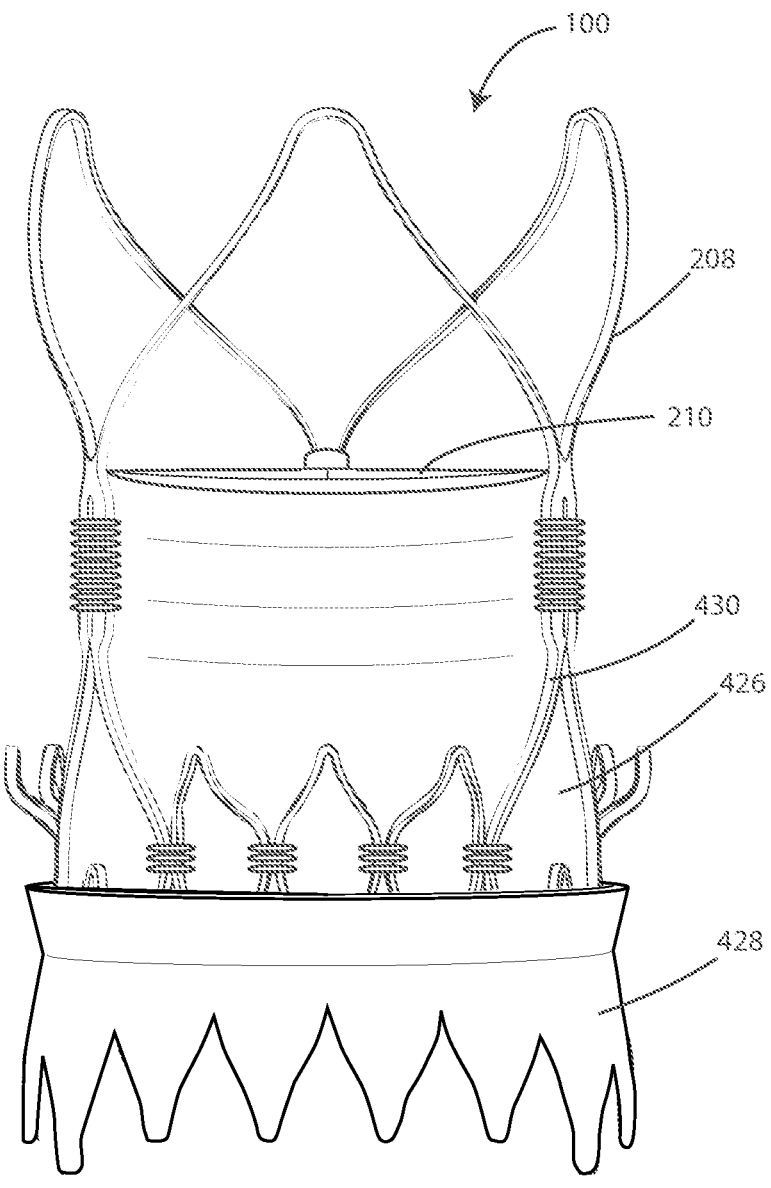
FIG. 4 is a view of a prosthetic heart valve in accordance with various embodiments herein.

Referring now to FIG. 4, a view of a prosthetic heart valve 100 is shown in accordance with various embodiments herein. The heart valve 100 includes a frame 208 and one or more valve leaflets 210. In various embodiments, the heart valve 100 can also include a skirt, such as an outer skirt 428 and/or an inner skirt 426. In various embodiments, the leaflets and/or the skirt can include an animal tissue, for example, pericardial tissue. In some embodiments, the skirt can include polyurethane material or polyethylene terephthalate. The frame 208 can include a plurality of struts 430.

In various embodiments, the inner skirt 426, if provided, can be disposed on a luminal surface of the frame 208. The inner skirt 426 can direct blood flowing through the valve 100. The inner skirt 426 can ensure the blood flows through the central lumen of the valve 100 and does not flow around the leaflets 210 in a closed configuration during diastolic pressure, such as when the valve is configured as an aortic valve. A portion of each leaflet, such as along the root edge, may be coupled to or sutured to the inner skirt 426.

In various embodiments, the implantable valve 100 can include an outer skirt 428 disposed on an abluminal surface of the frame 208. The abluminal surface of the frame 208 can be a surface of the frame 208 that is external to the central lumen. An outer skirt can be disposed between the frame 208 and the vessel wall when the valve is implanted, such as shown in FIG. 2, in order to prevent blood from flowing around the valve 100 (e.g. to prevent so-called para-valve leakage).

In various embodiments, with both the inner skirt 426 and outer skirt 428, the skirts 426, 428 can be coupled together, such as sutured together, along one or more continuous lines of attachment (not shown), optionally through apertures of the frame.

Figure 5:
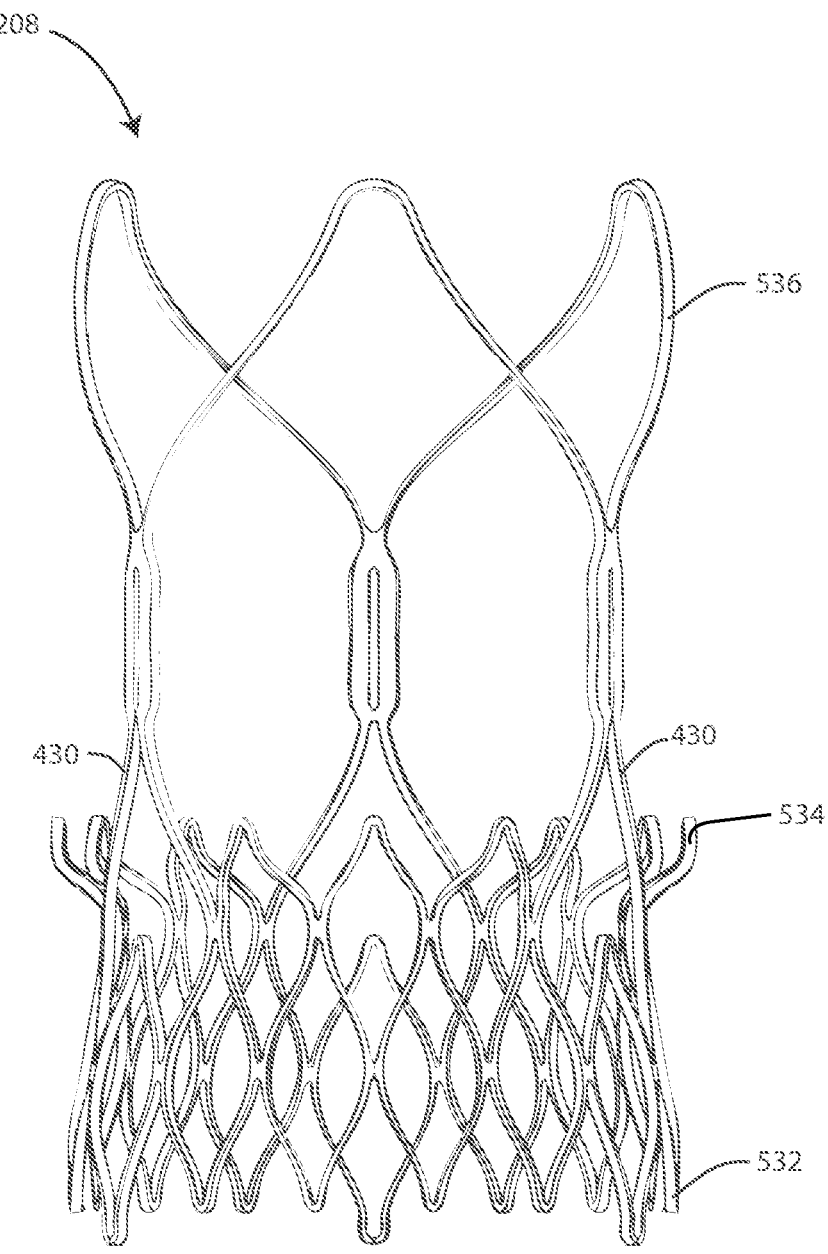
FIG. 5 is a view of a frame in accordance with various embodiments herein.

Referring now to FIG. 5, a view of a frame is shown in accordance with various embodiments herein. The frame 208 can include a lower crown 532. The frame 208 can include an upper crown 534. The frame 208 can include a plurality of stabilization arches 536. The frame 2018 can include one or more valve supports, such as struts 430. In various embodiments, the frame 208 can include a self-expanding stent.

The frame 208 can also include a plurality of struts 430. The struts 430 can be rods, bars, plates, or other projections that define a framework or lattice structure. In some embodiments, the frame can define open spaces between the frame struts 430. However, in other embodiments the frame may not include such open spaces.

The frame 208 can be formed of many different materials. In some embodiments, the frame 208 can include a polymer, a metal, a ceramic, a composite, or the like. In various embodiments, the metal can include or be an elemental metal or an alloy. In various embodiments, the elemental metal can include or be aluminum or titanium. In various embodiments, the alloy can include or be stainless steel, nitinol or a ferrous metal. In some embodiments, the frame 208 can include shape-memory material, such as a shape-memory alloy.

In some embodiments, the inner skirt 426 can be coupled to the lower crown 532 and/or the upper crown 534 and/or the valve supports. In other embodiments, the inner skirt 426 is only coupled to the upper crown 534. In some embodiments, the outer skirt can be coupled to the lower crown 532 and/or the upper crown 534. In other embodiments, the outer skirt is only coupled to the lower crown 532. In some embodiments, the valve leaflets 210 can be coupled to the frame, such as to the valve supports, at a position that is at or just below the stabilization arches 536 and above the upper crown 534. In some embodiments, the valve leaflets 201 can be coupled to the inner skirt 426, such as in the region of the valve supports and the upper crown 534.

Figure 6:
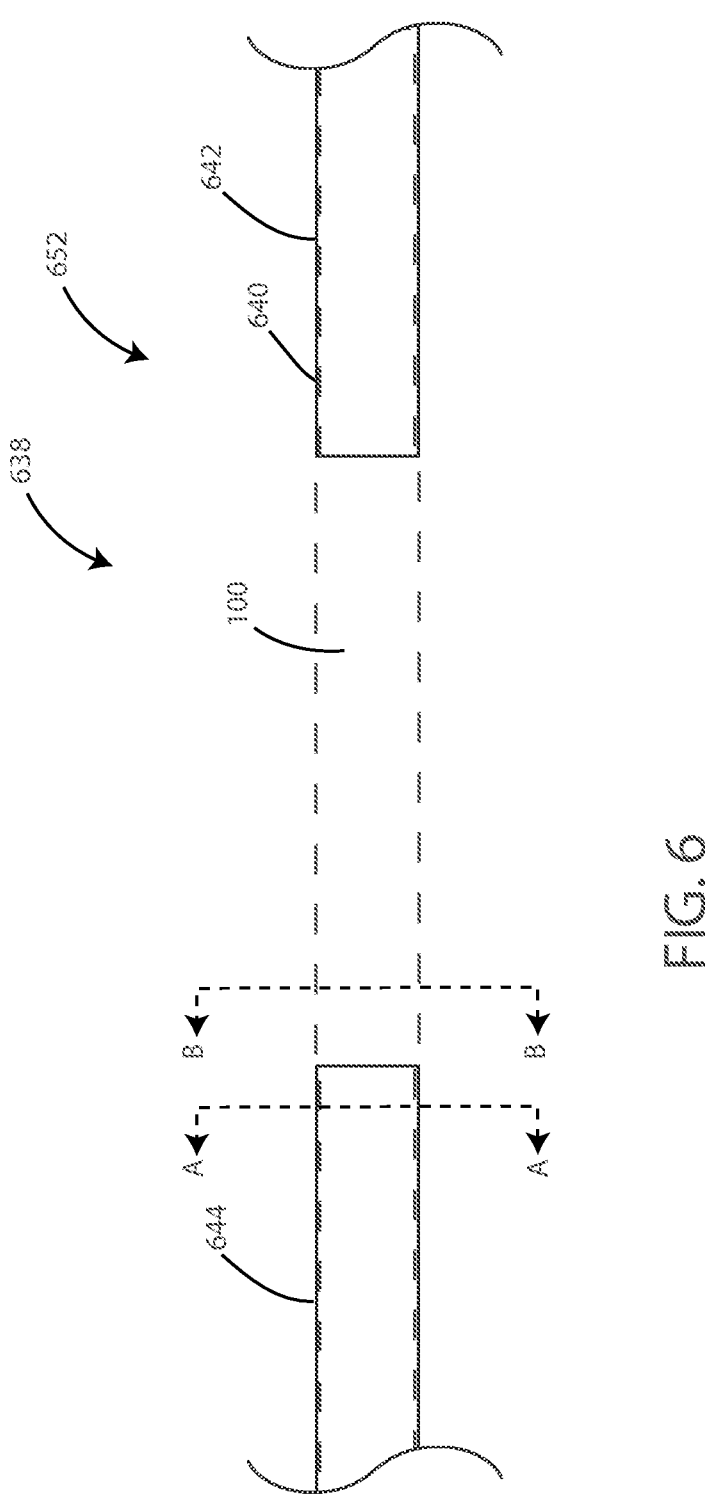
FIG. 6 is a schematic view of a portion of a heart valve replacement system in accordance with various embodiments herein.
Figure 7:
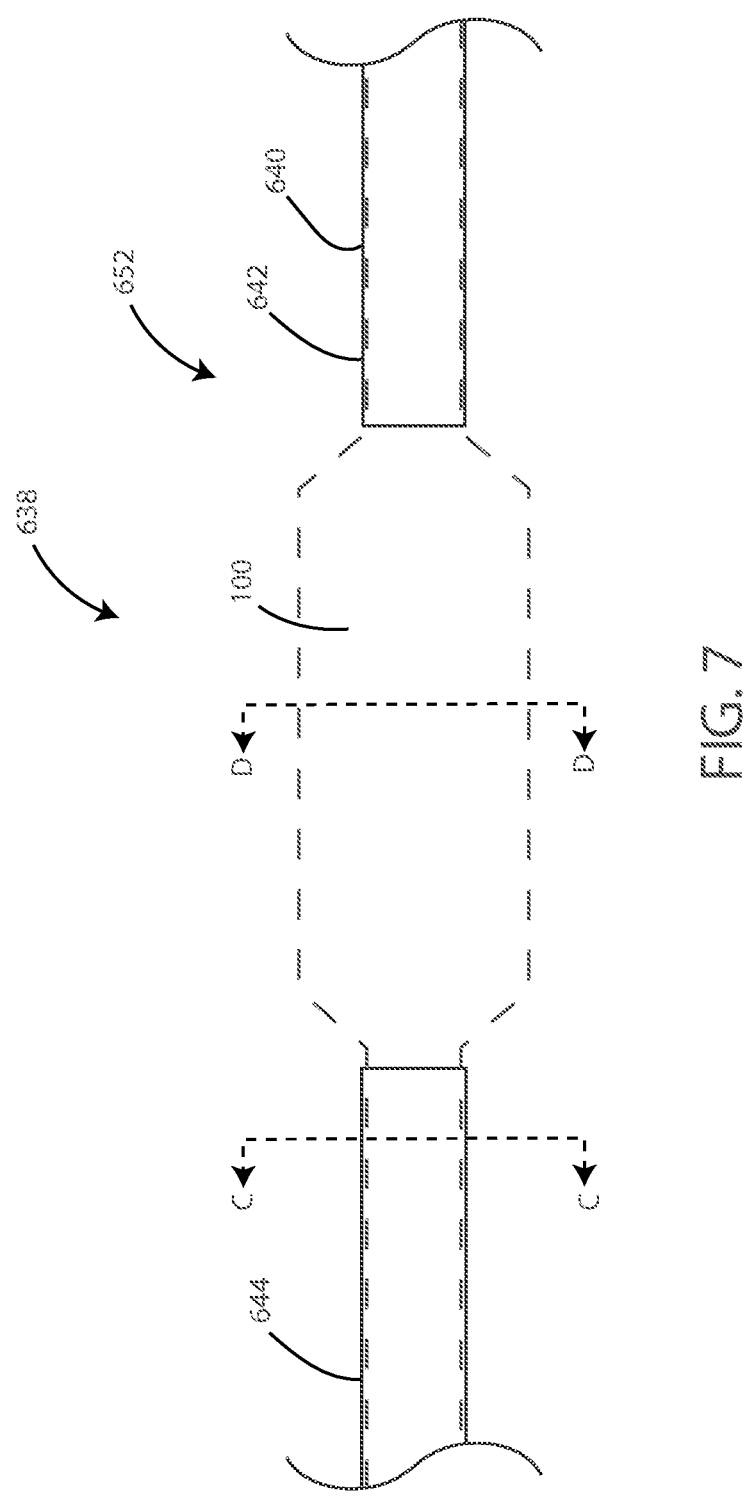
FIG. 7 is a schematic view of a portion of a heart valve replacement system in accordance with various embodiments herein.

Referring now to FIG. 6 and FIG. 7, schematic views of a heart valve replacement system 638 are shown. It will be appreciated that FIGS. 6-7 are shown as simplified schematic views for ease and clarity of illustration. In FIG. 6, a view of a heart valve replacement system 638 is shown in accordance with various embodiments herein. In some embodiments, the heart valve replacement system 638 can include a delivery catheter 106. FIG. 6 shows a valve 100 in a crimped state, and/or fully loaded state, on the delivery catheter 106. The valve 100 can be disposed on or around a heart valve accommodation region 652 of the delivery catheter 106.

In some embodiments, the heart valve replacement system 638 can include a sheath 640. In various embodiments, the sheath 640 can be disposed over at least a portion of the heart valve 100. In various embodiments, the sheath 640 has an inner diameter (described further below) of 22 F, 20 F, 18 F, 16 F, or smaller, or an inner diameter falling within a range between any of the foregoing.

In some embodiments, the sheath 640 can include a first sheath portion 642 and a second sheath portion 644. In some embodiments, the first sheath portion 642 and the second sheath portion 644 can be spaced apart, such as in the fully loaded state. In some embodiments, a portion of a skirt can be exposed between the first sheath portion 642 and the second sheath portion 644. In use, the sheath portions 642 and 644 can be opened by being displaced axially in opposite directions to release the replacement valve at an implantation site.

Referring now to FIG. 7, a view of portions of a heart valve replacement system 638 is shown in accordance with various embodiments herein. FIG. 7 shows the valve 100 in a non-fully or partially crimped state on the delivery catheter 106. Alternatively, in another embodiments, in a non-fully or partially crimped state, one end of the heart valve 100 may be captive within the sheath 640, such as within one of the sheath portions 642 and 644, and the other end of the heart valve 100 may be exposed or non-captive.

Referring now to FIG. 8, a schematic cross-sectional view of a heart valve replacement system 638 is shown in accordance with various embodiments herein. In some embodiments, FIG. 8 can represent a cross-sectional view of the heart valve replacement system 638 shown in FIG. 6 along cross-section A-A or a cross-sectional view of the heart valve replacement system 638 shown in FIG. 7 along cross-section C-C. In some embodiments, FIG. 8 can also represent a cross-sectional view of the heart valve replacement system 638 shown in FIG. 6 along cross-section B-B with the exception that FIG. 8 shows a sheath 640.

The heart valve replacement system 638 can include a delivery catheter 106, a heart valve 100, and a sheath 640. The heart valve 100 can be disposed on or around the delivery catheter 106. The heart valve 100 can be fully crimped on the delivery catheter 106. The sheath 640 can extend over at least a portion of the heart valve 100 and at least a portion of the delivery catheter 106.

The heart valve replacement system 638 can include a sterile package 846. While package 846 is shown in this view schematically in a box-like form, it will be appreciated that the package can take on various forms including flexible or non-flexible packages that can include pouches, trays, bags, boxes, cartons, containers, and the like. In some embodiments, the package 846 can be hermetically sealed. In some embodiments, the package 846 can be breathable packaging that prevents ingress of bacteria. The heart valve 100, the delivery catheter 106 and the sheath 640 can be disposed within the package 846. In various embodiments, the delivery catheter 106 includes a guidewire lumen 848.

The outside waist diameter 854 can be a portion of the heart valve 100 that is covered by the sheath 640. The outside waist diameter 854 of the heart valve 100 can have a diameter of various dimensions. In some embodiments, the outside waist diameter 854 can be greater than or equal to about 0.3 mm, 0.5 mm, 1 mm, 2 mm, 3 mm, 4 mm, 5 mm, 6 mm, 7 mm, 8 mm, 9 mm, 10 mm, 11 mm, 11 mm, 12 mm, 12 mm, 13 mm, 14 mm, 14 mm, 15 mm, 15 mm, or 16 mm. In some embodiments, the diameter can be less than or equal to 20 mm, 19 mm, 18 mm, 17 mm, 16 mm, 15 mm, 14 mm, 13 mm, 12 mm, 11 mm, 10 mm, 9 mm, 8 mm, 7 mm, or 6 mm. In some embodiments, the diameter can fall within a range of 0.3 mm to 20 mm, 1 mm to 20 mm, 2 mm to 20 mm, 3 mm to 20 mm, 4 mm to 20 mm, 5 mm to 20 mm, 6 mm to 20 mm, or 7 mm to 20 mm, or 7 mm to 19 mm, or 8 mm to 19 mm, or 8 mm to 18 mm, or 9 mm to 18 mm, or 9 mm to 18 mm, or 10 mm to 17 mm, or 11 mm to 17 mm, or 15 mm to 16 mm, or can be about 16 mm.

The inner diameter 852 of the sheath 640 can have a diameter of various dimensions. In some embodiments, the inner diameter 852 can be less than or equal to 20, 18, 16, 14, 12, 10, 8, or 6 French, or can be an amount falling within a range between any of the foregoing values.

Referring now to FIG. 9, a schematic cross-sectional view of a heart valve replacement system 638 is shown in accordance with various embodiments herein. In some embodiments, FIG. 9 can represent a cross-sectional view of the heart valve replacement system 638 shown in FIG. 6 along cross-section A-A or a cross-sectional view of the heart valve replacement system 638 shown in FIG. 7 along cross-section C-C. In some embodiments, FIG. 9 can also represent a cross-sectional view of the heart valve replacement system 638 shown in FIG. 6 along cross-section B-B with the exception that FIG. 9 shows a sheath 640.

In some embodiments, the heart valve replacement system 638 can include a heart valve 100 that is partially crimped on to a delivery catheter 106. The partially crimped heart valve 100 and the delivery catheter 106 can be disposed within a sheath 640. The sheath 640, the heart valve 100, and the delivery catheter 106 can be disposed within a sterile package 846.

In some embodiments, the heart valve 100 can be partially crimped onto the delivery catheter, such that a gap 956 is defined between at least portions of the heart valve 100 and the delivery catheter 106. In some embodiments, the gap 956 can have a consistent size around the delivery catheter 106. In some embodiments, the gap 956 can vary in size around the delivery catheter 106. A partially crimped heart valve 100 can have a smaller outside waist diameter 854 than a fully expanded or uncrimped heart valve 100. The partially crimped heart valve 100 can have a larger outside waist diameter 854 than a fully crimped heart valve 100.

Referring now to FIG. 10, a schematic cross-sectional view of a heart valve replacement system 638 is shown in accordance with various embodiments herein. In some embodiments, FIG. 10 can also represent a cross-sectional view of the heart valve replacement system 638 shown in FIG. 6 along cross-section D-D.

In some embodiments, the heart valve replacement system 638 can include a heart valve 100 that is disposed on or around a portion of the delivery catheter 106. The heart valve 100 can be uncrimped and the heart valve replacement system 638 can be disposed in a sterile package 846. The heart valve 100 can be uncrimped and define a gap 956 between the heart valve 100 and the delivery catheter 106. In some embodiments, the gap 956 can have a uniform shape and size. In some embodiments, the gap 956 can have a varying shape and size. The gap 956 for an uncrimped heart valve 100 can be larger than the gap 956 for a partially crimped heart valve 100, such as shown by comparing FIG. 9 and FIG. 10.

Figure 11:
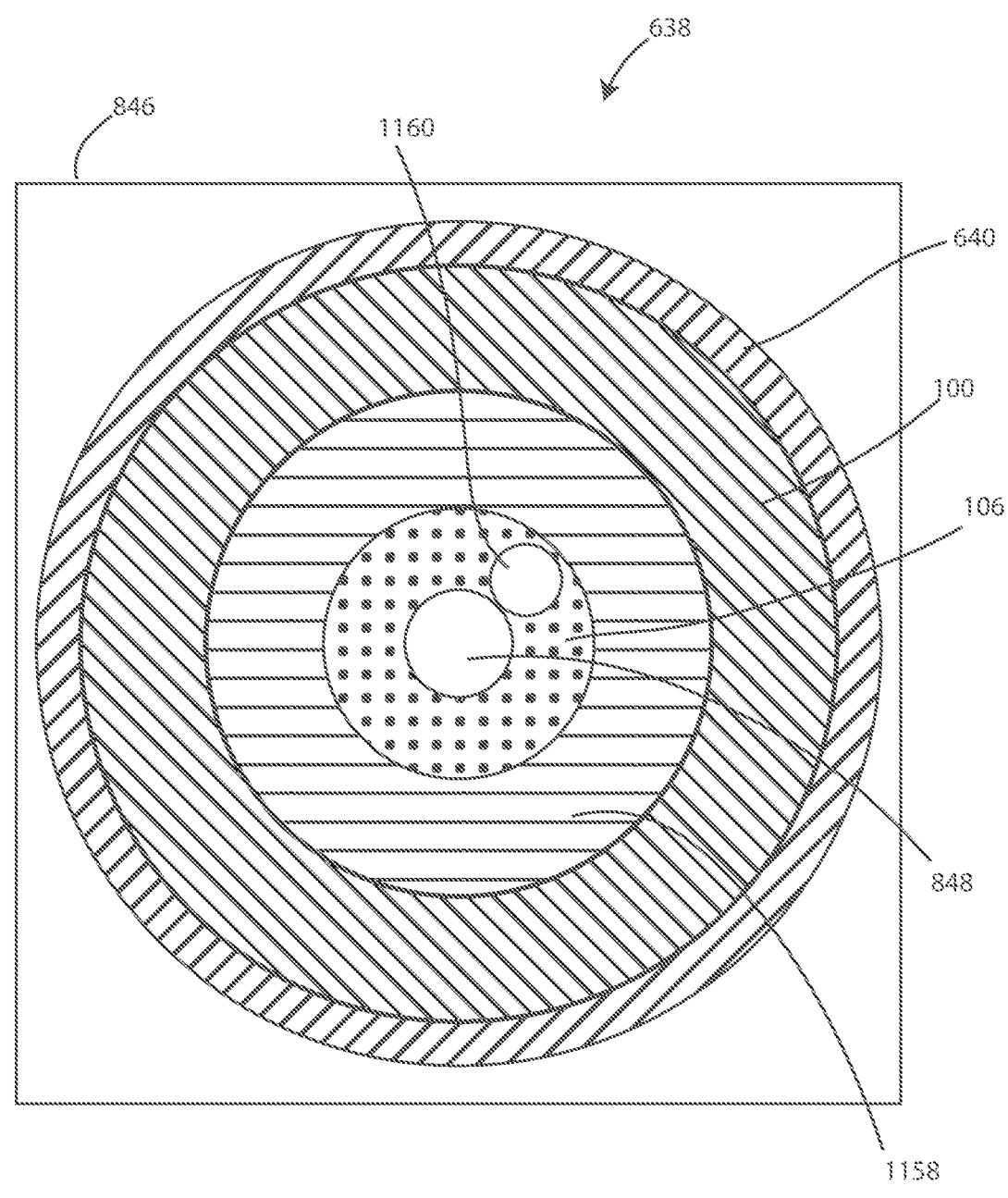
FIG. 11 is a schematic cross-sectional illustrative view of a heart valve replacement system in accordance with various embodiments herein.
Figure 12:
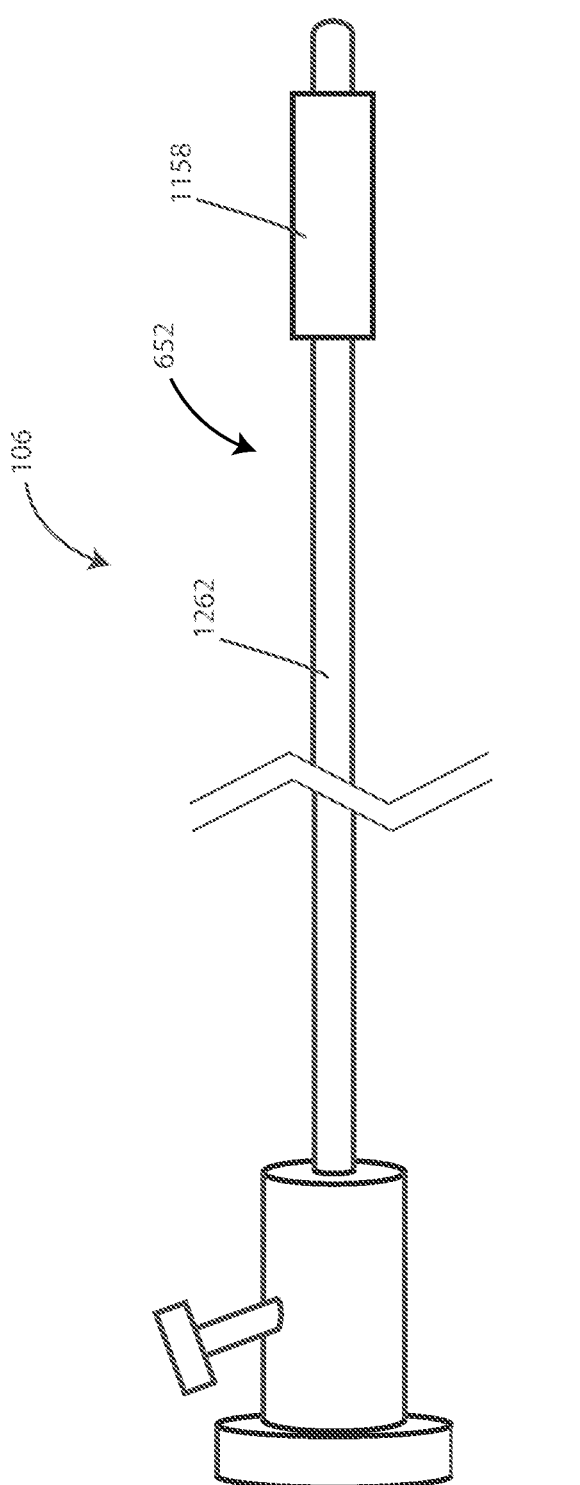
FIG. 12 is a schematic view of a delivery catheter in accordance with various embodiments herein.

Referring now to FIG. 11, a schematic cross-sectional view of a heart valve replacement system 638 is shown in accordance with various embodiments herein. In some embodiments, the heart valve replacement system 638 can include a delivery catheter 106 with a balloon 1158. In various embodiments, the balloon 1158 can be disposed on the shaft of the delivery catheter 106, such as shown in FIG. 12. The heart valve replacement system 638 can include a heart valve 100 disposed on or around a portion of the balloon 1158. The delivery catheter 106 can include a guidewire lumen 848 and/or a balloon inflation lumen 1160. In various embodiments, the balloon 1158 can be in fluid communication with the balloon inflation lumen 1160.

The balloon inflation lumen 1160 can be configured to direct liquid or gas into the balloon, such as to inflate the balloon 1158. The balloon 1158 can be inflated once the heart valve 100 is located in its desired location. The balloon 1158 can be inflated to expand the heart valve 100. The balloon 1158 can be deflated and the heart valve 100 can remain in the expanded state in the desired location within the patient.

Referring now to FIG. 12, a schematic view of a delivery catheter 106 is shown in accordance with various embodiments herein. As discussed above, in some embodiments, the heart valve replacement system can include a delivery catheter 106. The delivery catheter 106 can include a shaft 1262. The delivery catheter 106 can include a heart valve accommodation region 652. The heart valve accommodation region 652 can be configured to receive a heart valve. The delivery catheter 106 can also include a balloon 1158. In some embodiments, the balloon 1158 is distal relative to the heart valve accommodation region 652. In some embodiments, the balloon 1158 forms a part of the heart valve accommodation region 652. In some embodiments, the delivery catheter 106 can be configured as a transfemoral delivery catheter. While FIG. 11 and FIG. 12 depict a balloon catheter, it will be appreciated that in some embodiments a delivery catheter herein may not include a balloon. In some embodiments, a frame of the heart valve can be self-expanding. In some embodiments, other mechanical devices can be used to expand the heart valve into position.

Methods

Figure 13:
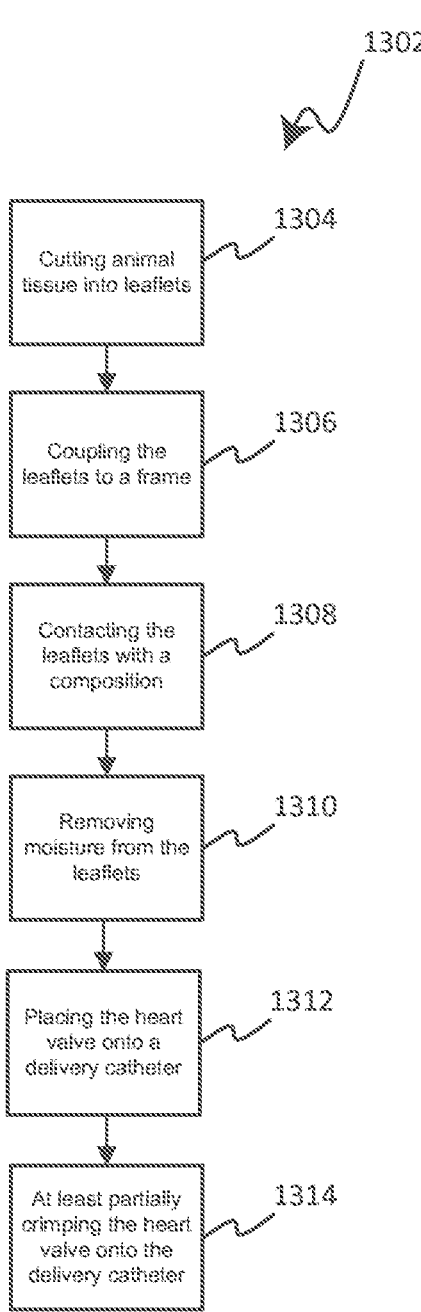
FIG. 13 is a flow chart depicting a method in accordance with various embodiments herein.

Referring now to FIG. 13, a flowchart depicting a method is shown in accordance with various embodiments herein. FIG. 13 shows a method of making 1302 a heart valve replacement device. The method can include an operation of cutting 1304 animal tissue into leaflets, skirts, or other components. The method can include an operation of coupling 1306 the leaflets and/or the skirt to a frame to form a heart valve. The method can include an operation of contacting 1308 the leaflets, skirt, and/or other animal tissue with a composition comprising glycerol. In some embodiments, the composition can specifically be or include a solution.

The method can include an operation of removing 1310 moisture from the leaflets, skirt, or other animal tissue in an environment at or above room temperature, and/or below atmospheric pressure. In some embodiments, removing 1310 moisture can take place after the operation of coupling 1306 the leaflets and/or the skirt to a frame to form a heart valve. While not intending to be bound by theory, it is believed that coupling procedures (such as, but not limited to, suturing) can be executed more effectively if moisture has not yet been removed due to one or more of dimensional changes, material properties, and the like. However, in some embodiments, removing 1310 moisture can take place before the operation of coupling 1306 the leaflets and/or the skirt to a frame to form a heart valve.

In some embodiments, removing the moisture from the leaflets and/or other animal tissue can include drying the tissue in an oven. In an embodiment, the leaflets and/or other animal tissue can be in an environment of about 37° C. In various embodiments, room temperature can be at least 15° C. and not more than 50° C. In various embodiments, the leaflets have a water content of about 15 to 50 wt. % and a glycerol content of about 20 to about 70 wt. % after removing moisture.

In some embodiments, the leaflets and/or skirt can have a final water content once the moisture is removed of about 10 to 40 wt. %, or about 15 to 30 wt. %, or about 30 to 50 wt. %, or about 17.5 to 22.5 wt. %, or about 20 wt. %. In some embodiments, the leaflets and/or skirt can have a final glycerol content of about 30 to about 65 wt. % after removing moisture. In some embodiments, the leaflets and/or skirt can have a final glycerol content of about 15 to about 30 wt. % after removing moisture. In some embodiments, the leaflets and/or skirt can have a final glycerol content of about 40 to about 60 wt. % after removing moisture. In some embodiments, the leaflets and/or skirt can have a final glycerol content of about 40 to about 50 wt. % after removing moisture.

The method can include an operation of placing 1312 the heart valve on a delivery catheter. The method can include an operation of at least partially crimping 1314 the heart valve onto the delivery catheter and/or pre-attaching the heart valve to the delivery catheter. In some embodiments, the method can include fully crimping the heart valve 100 onto the delivery catheter 106.

In various embodiments, the method can also include packaging the heart valve 100 and the delivery catheter 106. In some embodiments, the heart valve 100 remains uncrimped prior to packaging of the heart valve 100 and delivery catheter 106.

In some embodiments, the leaflets can have a water content of about 15 to about 50 wt. % and a glycerol content of about 20 to about 70 wt. % after being packaged.

In various embodiments, the operation of contacting the leaflets with a composition that includes glycerol and drying the leaflets is performed before the step of attaching the leaflets to a frame 208 to form a heart valve 100.

In various embodiments, the method can further include placing a sheath 640 over the heart valve 100 and the delivery catheter 106, such as prior to packaging the heart valve 100 and the delivery catheter.

In various embodiments, the method can further include coupling a skirt to the frame. The method can further include contacting the skirt with a composition that can include glycerol. In some embodiments, the composition can be the same as the composition that contacts the leaflets. The method can further include removing moisture from the skirt in an environment at or above room temperature and/or below atmospheric pressure, such as similarly to the moisture removal from the leaflets.

Animal Tissue

In various embodiments, the leaflets, and the skirt (the inner skirt and/or the outer skirt) can include an animal tissue. In various embodiments, the animal tissue can include at least one of porcine tissue and bovine tissue. In some embodiments, the animal tissue may include pericardial tissue. In various embodiments, the animal tissue can include at least about 0.15% by weight of a cation of a salt. In various embodiments, the animal tissue can include at least about 0.3% by weight of a cation of a salt. In various embodiments, the cation can include at least one of sodium, potassium, calcium and magnesium.

In various embodiments, the heart valve 100 further can include a skirt. The skirt can include an animal tissue. In various embodiments, the animal tissue can include from 15% to 50% by weight water; and from 20% to 70% by weight glycerol. In some embodiments, isotonic aqueous glycerol can be used, such as to mimic the physiological environment.

The animal tissue can include various amounts of glycerol. In some embodiments, the amount of glycerol can be greater than or equal to 15 wt. %, 20 wt. %, 25 wt. %, 30 wt. %, 35 wt. %, or 40 wt. %. In some embodiments, the amount of glycerol can be less than or equal to 60 wt. %, 56 wt. %, 52 wt. %, 48 wt. %, 44 wt. %, or 40 wt. %. In some embodiments, the amount of glycerol can fall within a range of 15 wt. % to 60 wt. %, or 20 wt. % to 56 wt. %, or 25 wt. % to 52 wt. %, or 30 wt. % to 48 wt. %, or 35 wt. % to 44 wt. %, or can be about 40 wt. %.

Composition

As discussed above, the leaflets and/or the skirt can be contacted or submerged in a composition that includes glycerol. In some embodiments, contacting the leaflets and/or the skirt with a composition can include spraying or pouring the composition onto the leaflets. In some embodiments, the leaflets and/or the skirt can be contacted or submerged in the composition multiple times. In some embodiments, the leaflets and/or the skirt are in contact with the composition until the tissue and the composition stabilize, such as obtaining an equilibrium inside the tissue. In some embodiments, the leaflets and/or the skirt are in contact with the composition for at least 2 hours, at least 3 hours, at least 4 hours, at least 5 hours, at least 6 hours, at least 7 hours, at least 8 hours, at least 9 hours, or at least 10 hours. In some embodiments, the leaflets and/or the skirt are in contact with the composition for not more than 36 hours, not more than 24 hours, not more than 22 hours, not more than 20 hours, not more than 18 hours, not more than 16 hours, not more than 14 hours, not more than 12 hours, not more than 11 hours, not more than 10 hours, not more than 9 hours, not more than 8 hours, not more than 7 hours, not more than 6 hours, not more than 5 hours, not more than 4 hours, or not more than 3 hours. It should be understood that the leaflets and/or the skirt can be in contact with the composition for a time period that is bounded by any two of the boundaries listed above.

In various embodiments, the composition can include a mixture of glycerol and a solvent, such as ethanol and/or water. In various embodiments, the composition can include a glycerol, water and sodium mixture. In various embodiments, the composition can include a glycerol and ethanol mixture. In various embodiments, the composition can include a glycerol, water and ethanol mixture. In various embodiments, the composition can include glycerol, water, ethanol and sodium.

In various embodiments, the amount of glycerol in the composition can be about 30, 40, 50, 60, 70, 80, 90, 95 or 98 percent by weight, or an amount falling within a range between any of the foregoing. In various embodiments, the amount of solvent in the composition can be about 10, 20, 30, 40, 50, 60, or 70 percent by weight, or an amount falling within a range between any of the foregoing.

In various embodiments, the amount of salt (such as a sodium salt) in the composition can be about 0, 0.1, 0.2, 0.5, 1, 1.5, 2, 2.5, 3, 4, 5, 6, 7, 8, 9, 10, 11, 13, 15, 17, 20, 25, or 30 percent by weight, or an amount falling within a range between any of the foregoing. In some embodiments the amount of salt in the composition can be sufficient such that the composition has a physiologic osmolarity and/or can be isotonic with blood. In various embodiments, the amount of ethanol in the composition can be about 0, 1, 3, 5, 10, 20, 30, 40, or 50 percent by weight, or an amount falling within a range between any of the foregoing.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

As used herein, the recitation of numerical ranges by endpoints shall include all numbers subsumed within that range (e.g., 2 to 8 includes 2.1, 2.8, 5.3, 7, etc.).

The headings used herein are provided for consistency with suggestions under 37 CFR 1.77 or otherwise to provide organizational cues. These headings shall not be viewed to limit or characterize the invention(s) set out in any claims that may issue from this disclosure. As an example, although the headings refer to a "Field," such claims should not be limited by the language chosen under this heading to describe the so-called technical field. Further, a description of a technology in the "Background" is not an admission that technology is prior art to any invention(s) in this disclosure. Neither is the "Summary" to be considered as a characterization of the invention(s) set forth in issued claims.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

The invention claimed is:

1. A method of making a heart valve replacement device comprising:

cutting animal tissue into leaflets;

coupling the leaflets to a frame to form a heart valve;

contacting the leaflets with a composition comprising glycerol;

removing moisture from the leaflets in an environment at above room temperature and/or below atmospheric pressure; and placing the heart valve on a delivery catheter;

wherein coupling the leaflets to the frame occurs prior to removing moisture from the leaflets in the environment at above room temperature and/or below atmospheric pressure;

wherein the leaflets of the heart valve are glutaraldehyde-free when placed on the delivery catheter.

2. The method of claim 1, wherein the composition comprises at least 50% glycerol by weight.

3. The method of claim 2, wherein the composition comprises no more than 98% glycerol by weight.

4. The method of claim 3, wherein the composition comprises at least 70% glycerol by weight.

5. The method of claim 4, wherein the composition comprises at least 90% glycerol by weight.

6. The method of claim 2, wherein the composition comprises glycerol and water.

7. The method of claim 6, wherein the composition further comprises sodium.

8. The method of claim 2, further comprising at least partially crimping the heart valve onto the delivery catheter.

9. The method of claim 8, further comprising packaging the heart valve and the delivery catheter into a package.

10. The method of claim 1, wherein the leaflets have a water content of about 15 to 50 wt. % and a glycerol content of about 20 to about 70 wt. % after removing moisture.

11. The method of claim 1, further comprising coupling an inner skirt to the frame;

contacting the inner skirt with a composition comprising glycerol;

removing moisture from the inner skirt in an environment at above room temperature and/or below atmospheric pressure.

12. The method of claim 11, further comprising coupling an outer skirt to the frame;

contacting the outer skirt with a composition comprising glycerol;

removing moisture from the outer skirt in an environment at above room temperature and/or below atmospheric pressure.

13. The method of claim 1, further comprising disposing a sheath over the heart valve and at least a portion of the delivery catheter.

14. The method of claim 13, wherein an outside waist diameter of the sheath is less than 15 mm.

15. The method of claim 14, wherein the sheath has an inner diameter of 18 F or smaller.

16. The method of claim 13, further comprising packaging the heart valve, sheath, and the delivery catheter into a package.

17. The method of claim 1, wherein the delivery catheter comprises a balloon.

18. The method of claim 17, wherein the delivery catheter defines an inflation lumen.

19. The method of claim 17, wherein the balloon is distal relative to the heart valve.

20. The method of claim 1, wherein the heart valve is an aortic heart valve.

* * * * *